United States Patent [19]

Wehrli et al.

[11] Patent Number: 5,314,483
[45] Date of Patent: May 24, 1994

[54] MENISCUS PLATFORM FOR AN ARTIFICIAL KNEE JOINT

[75] Inventors: Ueli Wehrli, Wabern; Walter Moser, Herrenschwanden, both of Switzerland

[73] Assignee: Protek AG, Muensingen-Bern, Switzerland

[21] Appl. No.: 983,941

[22] Filed: Dec. 1, 1992

[30] Foreign Application Priority Data

Jan. 14, 1992 [CH] Switzerland .................. 00091/92

[51] Int. Cl.⁵ .............................................. A61P 2/38
[52] U.S. Cl. ........................................ 623/20; 623/18
[58] Field of Search ............................ 623/16, 18, 20

[56] References Cited

U.S. PATENT DOCUMENTS

| | | | |
|---|---|---|---|
| 4,136,405 | 1/1979 | Pastrick et al. | 623/20 |
| 4,224,697 | 9/1980 | Murray | 623/20 |
| 4,262,368 | 4/1981 | Lacey | 623/20 |
| 4,547,910 | 10/1985 | Roberts et al. | 623/18 |

FOREIGN PATENT DOCUMENTS

| | | | |
|---|---|---|---|
| 0021421 | 1/1981 | European Pat. Off. | 623/20 |
| 0183670 | 6/1986 | European Pat. Off. | 623/20 |
| 3528204 | 2/1986 | Fed. Rep. of Germany | 623/20 |
| 34332614 | 3/1986 | Fed. Rep. of Germany | 623/20 |

*Primary Examiner*—David Isabella
*Attorney, Agent, or Firm*—Townsend and Townsend, Khourie and Crew

[57] ABSTRACT

With the invention is shown an artificial knee joint, in which the rear cruciate ligament and the collateral ligaments are assumed as being retained. A metal platform is attached to the tibia and perpendicular to the tibia axis has a plane surface, on which three slide members are slidably disposed so as to guide the metal platform relative to the femur condyles made of metal within the limits of the degree of freedom remaining to them under the tension of the ligaments. A central slide member forms an eminentia rotatable around a pin, which guides the femur condyles directly or indirectly with respect to rotation around the tibia axis and which along its median line, which extends in the sagittal direction in the non-rotated central position, forms a direct or indirect longitudinal guiding device for the femur condyles, while the flexion movement is guided at doubly curved femur condyles by the two outer slide members.

6 Claims, 2 Drawing Sheets

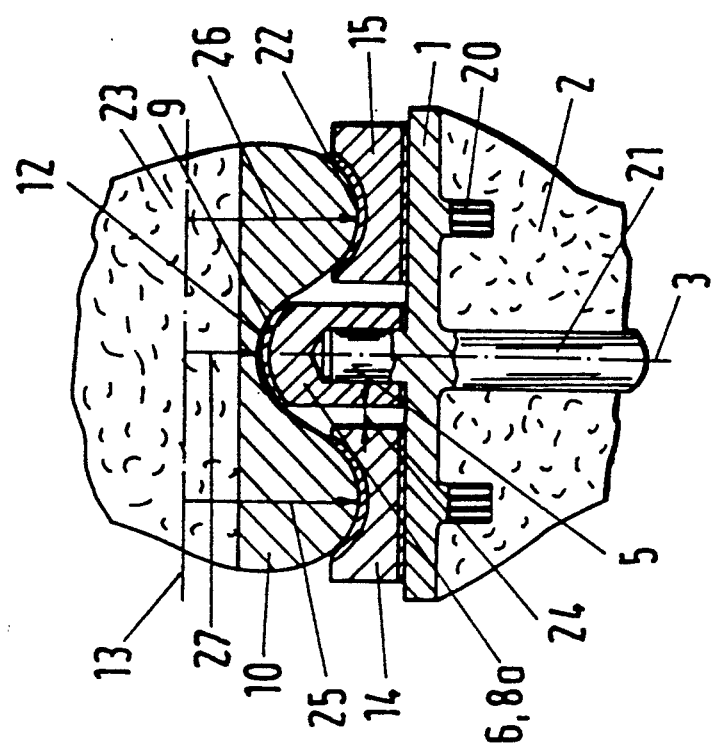
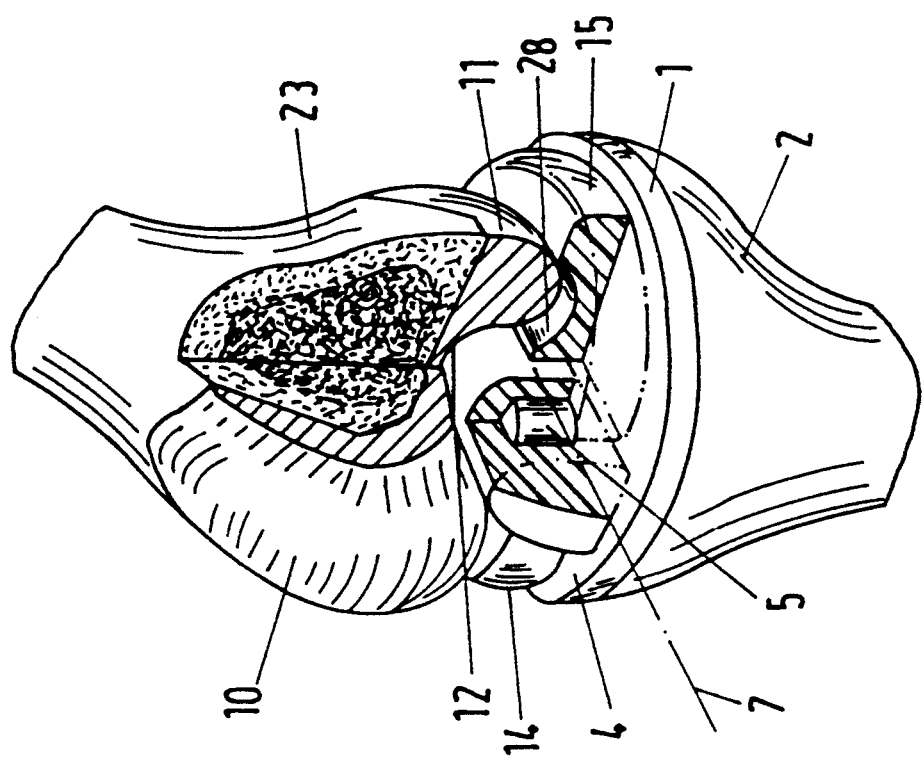

MENISCUS PLATFORM FOR AN ARTIFICIAL KNEE JOINT

BACKGROUND OF THE INVENTION

The invention relates to an artificial knee joint for a knee, in which the rear cruciate ligament and collateral ligaments are operative, consisting of a metal platform, which on its under side is connected via attachment members to the tibia, and consisting of metal femur condyles and one or several slide members, which transmit forces between the metal platform and the metal femur condyles.

The problems of and solutions for artificial knee joints are described in detail in U.S. Pat. No. 4,309,778. The solutions shown are supposed to imitate the movement mechanism of the natural knee joint and to make its design as safe as possible with respect to the guidance of the movable components. They require a corresponding large amount of space for safeguarding the guiding movement, around which a resection in the osseous tissue of the tibia bone has to be performed.

In the natural intact knee joint as a simplification three components of the relative movements between the femur and the tibia condyles can be identified:

Translational anterior-posterior movement (sliding)
Rolling of the femur condyles on the tibia condyles when the knee is flexed
Rotation of the tibia with respect to the femur around an axis parallel to the tibia axis.

To what extent these movements are possible after the implantation of a sliding prosthesis depends on the respective construction and condition of the ligaments and muscles. Prostheses subject to less constraint permit greater translational and rotatory movements of the tibia relative to the femur. Such "less constraint" prostheses are characterised by a slighter congruence of the femur and tibia condyles and a smaller intercondylar eminentia which restricts movement less.

With the construction having two separate tibial sliding members made from polyethylene described in U.S. Pat. No. 4,309,778, translational and rotatory movements are produced in the plane of the joint by the displacement of the tibial slide components guided in the groove-shaped rails. These guide rails are disposed on tracks having the shape of a circular segment. The sliding movement of the femur condyles on the tibia condyles required for knee flexion is performed between surfaces which are largely congruent to one another, with the supporting region decreasing as the rotation around the tibia axis and/or the translation at right angles to the tibia axis increase. However reduced congruence of the sliding surfaces is associated with greater surface pressure, may result in local overstressing, an increase in polyethylene abrasion and the rapid deterioration of the tibia condyles made of polyethylene. The "menisci" guided separately in the rails have slight lateral clearance so that they can be centered by this restricted free mobility with respect to the femur condyles. The movement of the polyethylene components in the grooves may be impeded by deposits, tissue cells and by polyethylene abrasion.

SUMMARY OF THE INVENTION

The object of the present invention is to produce congruent femur and tibia condyle pairs, to permit greater displacements and rotations between the femur and tibia and to keep the amount of osseous material at the tibia to be separated as small as possible without departing too much from the path of movement of the natural knee joint. This object is achieved with a platform which is attached to the tibia. The platform has a planar surface perpendicular to a tibia axis. A central sliding member is rotatably coupled to the platform for rotation about the tibia axis. Two outer sliding members are positioned on opposite sides of the central sliding member and are slidably disposed on the planar surface. Two femur condyles are attached to the femur and positioned against the outer sliding members.

By using three separately movable slide members the degrees of freedom for the guiding operation are disconnected and defined, congruent contact conditions are created between the femur and tibia. This has the advantage that largesurface contact conditions are achieved over the entire movement range and a sufficient knee joint stability is achieved. The small overall height on the tibia side enables the rear cruciate ligaments to be retained by the small resection amount without raising the joint plane to the collateral ligaments and to participate in the restriction of movement for the movable components similar to the natural knee and therefore fewer mechanical stops are required for guiding the moveable components with respect to one another. The restriction of the degree of freedom is achieved by the active structures (muscles) and passive structures (ligaments). Lower force peaks occur on the guide components, which has a favourable effect on the wear behaviour. The reduction in force peaks has a favourable effect on the primary attachment in the osseous tissue and prevents the loosening of fused prosthesis parts.

The invention is described below by means of an exemplified embodiment.

BRIEF DESCRIPTION OF THE DRAWING

FIG. 3 diagrammatically shows the view of a knee joint with the femur condyles being directly guided by the eminentia with respect to rotation around the tibia axis and with respect to displacement along the median line of the eminentia; and FIG. 4 diagrammatically shows the view of a section in the frontal plane for an arrangement as shown in FIG. 3.

DESCRIPTION OF THE PREFERRED EMBODIMENT

Figure 2:
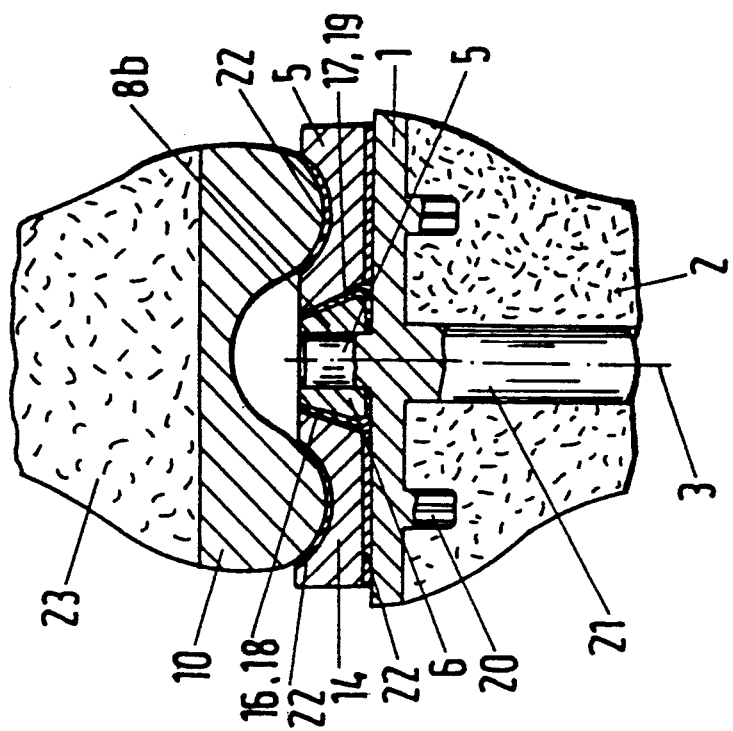
FIG. 2 diagrammatically shows the view of a section in the frontal plane for an arrangement as shown in FIG. 1.

In the figures is shown an artificial knee joint, in which the rear cruciate ligament and the collateral ligaments are assumed as being retained. A metal platform 1 is attached to the tibia 2 and perpendicular to the tibia axis has a plane surface 4, on which three slide members are disposed so that they can slide, so as to guide the metal platform 1 relative to the metal femur condyles 10, 11 within the limits of the degree of freedom remaining to them under the tension of the ligaments. A central slide member forms an eminentia 6 which can rotate around a pin 5 and which guides the femur condyles 10, 11 directly or indirectly with respect to rotation around the tibia axis and which along its median line 7, which extends in the sagittal direction in the nonrotated central position, forms a direct or indirect longitudinal guide for the femur condyles 10, 11. The flexion movement is guided on doubly curved femur condyles 14, 15 by the two outer slide members 14, 15. The position of the slide members with respect to the femur condyles and with respect to one another is governed by the congruence, i.e. the sliding surfaces of the condyle pair centering in one another.

Figure 1:
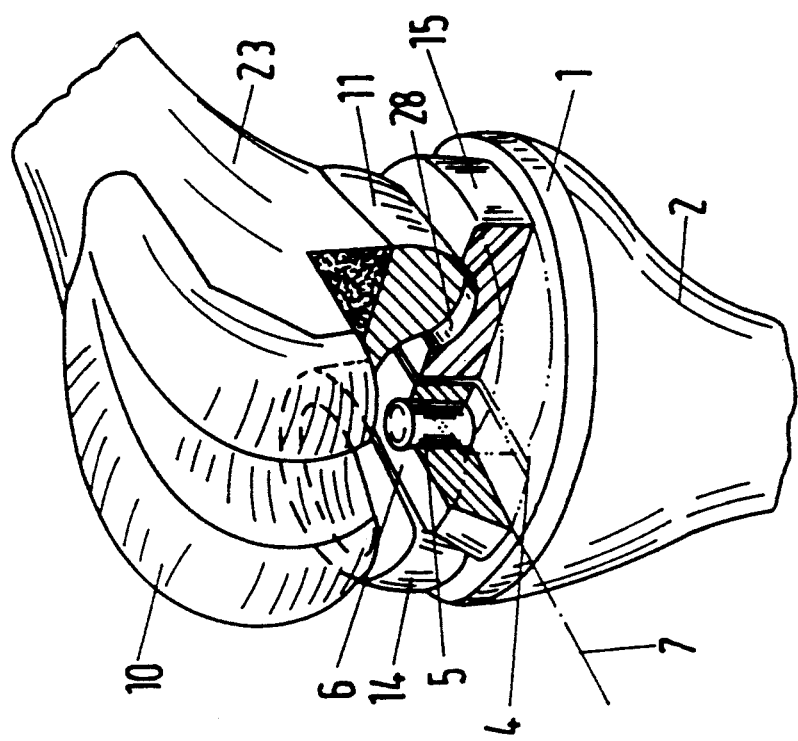
FIG. 1 diagrammatically shows the view of a knee joint with the femur condyles being indirectly guided by the eminentia with respect to rotation around the tibia axis and with respect to displacement along the median line of the eminentia.

FIGS. 1 and 2 show the metal femur condyles 10, 11 being indirectly guided by the eminentia 6 pivoted on the plane surface 4. In the center of the metal platform 1 a pin 5 protruding in the direction of the tibia axis 3 and is able to absorb the shearing forces in this plane surface 4. The eminentia 6 is designed as a bead 8b extending parallel to its median line 7, which comprises lateral surfaces 16, 17 parallel to the median line 7, against which the outer slide members 14, 15 abut with counter surfaces 18, 19. The metal femur condyles 10, 11 comprise doubly curved surfaces and via doubly curved counter surfaces 28 keep the outer slide members 14, 15 with constant spacing during flexion, which is dimensioned so that these surfaces abut the lateral surfaces 16, 17 of the eminentia 6 and are guided. The outer slide members 14, 15 can in this way be guided with plane faces at the eminentia 6 and at the plane surface 4. The plane guide surfaces of the slide members guarantee a trouble-free operation even in the event of tissue growth, while the doubly curved surfaces of the femur condyles 10, 11, which are sectors from a torus, for example, extend in counter surfaces 28, the size of which is unaltered. The deviations of position which result from manufacturing tolerances with congruence, i.e. with the optimal fit of the doubly curved bearing surfaces for the outer slide members, may be compensated with a clearance of 0.1 to 0.3 mm of the plane lateral surfaces 16, 17 of the eminentia 6 between the counter surfaces 18, 19. The same applies for deviations of position between the femur condyles 11, 12 because of elastic deformation of the femur side.

FIGS. 3 and 4 show the metal femur condyles 10, 11 being directly guided by the eminentia 6 pivoted on the plane surface 4, in the course of which in the middle of the metal platform 1 a pin 5 protrudes in the direction of the tibia axis 3, which engages in a bore of the eminentia 6 and which can absorb shearing forces in this plane surface 4. The eminentia is constructed as a bead 8a extending parallel to its median line, with the contours being produced by displacing a curved generatrix 9 parallel to the median line 7. The bead 8a engages in a guide channel 12 between the metal femur condyles 10, 11, with in each flexion angle the curved generatrix 9 for the guide channel 12 having the same axis of rotation 13 as the generatrices for the femur condyles. The difference in the condyle radii 25, 26 to the radius 27 of the generatrices 9 remains constant for all flexion angles. A sideways tilting of the metal femur condyles 10, 11 is prevented by the outer slide members 14, 15, which with their doubly curved counter surfaces 28 are guided by the doubly curved surfaces of the metal femur condyles 10, 11 in the plane surface 4 and are at a distance 24 from the eminentia.

This distance 24 is easily sufficient to intercept the deviations of position resulting from manufacturing tolerances and/or elastic deformation with the congruence of the doubly curved bearing surfaces between femur condyles 10, 11 and outer slide members 14, 15. Only when the ligaments relax and the distance between femur 23 and tibia 2 increases in the direction of the tibia axis 3 can the distance 24 be reduced so that a crude guiding operation can occur between eminentia and outer slide members 14, 15. Here too there is scarcely any opportunity for trouble caused by tissue growth. The counter surfaces 28 remain in contact with the femur condyles 10, 11 over practically their entire surface, the outer slide members move on plane faces and the guide channel 12 can not be blocked by tissue growth because of its open form.

With respect to the materials, metal femur condyles 10, 11 and a metal platform 1 are specified, which is supported with attachment members 20 in the form of pegs preventing rotation and with an attachment member 21 in the form of a central attachment pin in the tibia 2. As shown in FIG. 3 the eminentia 6 and the outer slide members 14, 15 may be made of plastic for the direct guiding function. It is also possible to manufacture the eminentia 6 from metal as in FIG. 1 for the indirect guiding operation and the outer slide members 14, 15 from plastic. FIGS. 2 and 4 show eminentia 6 and the outer slide members 14, 15 made from metal, in which case their sliding surfaces have surface layers 22 which result in a wear-resisting combination with their metal counter surfaces.

The large-surface contact between femur condyles 10, 11, the outer slide members 14, 15, the metal platform 1 and the eminentia 6 also enables the use of materials, apart from plastic, having higher E moduli, increased abrasion resistance and increased strength for eminentia and slide members. With higher-strength materials the overall height for eminentia 6 and outer slide members 14, 15 can be reduced and a smaller resection at the tibia can be performed by the same degree.

The figures do not show any patella prostheses as they are contained in the prior art mentioned at the beginning.

We claim:

1. A non-constrainde artificial knee joint comprising:
   a platform having a planar surface and an attachment member, the attachment member being adapted to be attached to a tibia having a tibia axis so that the planar surface is perpendicular to the tibia axis when the platform is attached to the tibia;
   first and second femur condyles adapted to be connected to a femur;
   a central slide member including means for rotatably coupling the central slide member to the platform for rotation about the tibia axis, the central slide member also having a median line extending in a sagittal direction when the central slide member is in a non-rotated central position; and first and second outer slide members positioned on and free to slide relative to the planar surface in at least a direction of the median line, the central slide member being positioned between the first and second outer slide members, and the first and second outer slide members being positioned against the first and second femur condyles, respectively.

2. An artificial knee joint according to claim 1, wherein:
   at least one of said first, second and central slide members is made of a plastic which can be tolerated by the body.

3. An artificial knee joint according to claim 1, wherein:
   the central slide member metal and have sliding surfaces with surface layers selected to form a wear-resistant combination with the platform and the first and second femur condyles.

4. An artificial knee joint according to claim 1, wherein:
   the central slide member further comprises a bead, which extends parallel to the median line, and a curved generatrix; and
   the first and second femur condyles include a guide channel therebetween, said curved generatrix being positioned against said guide channel, the curved generatrix having an axis of rotation which is the same as an axis of rotation of the first and second femur condyles in each flexion angle of the femur.

5. According to claim 1 wherein:
   the central sliding member further comprises first and second lateral surfaces each extending parallel to the median line; and
   the first and second outer slide members further comprise first and second counter surfaces, respectively, positioned against the first and second lateral surfaces, respectively so that the first and second slide members are free to slide against the planar surface in only the direction of the median line.

6. A non-constrainde artificial knee joint comprising:
   a platform having a surface and an attachment member, the attachment member being adapted to be attached to a tibia having a tibia axis so that the surface is substantially perpendicular to the tibia axis when the platform is attached to the tibia;
   first and second femur condyles adapted to be connected to a femur;
   a central slide member including means for rotatably coupling the central slide member to the platform for rotation about the tibia axis, the central slide member having a median line extending linearly in a sagittal direction when the central slide member is in a non-rotated central position; and
   first and second outer slide members positioned on and free to linearly slide relative to the surface, the central slide member being positioned between the first and second outer slide members, and the first and second outer slide members being positioned against the first and second femur condyles, respectively.

* * * * *